(12) United States Patent
Binder et al.

(10) Patent No.: US 10,959,449 B2
(45) Date of Patent: Mar. 30, 2021

(54) METHOD FOR EXTRACTING CONTAMINANTS FROM AGRARIAN PRODUCTS AND APPARATUS THEREFOR

(71) Applicant: ERBER AKTIENGESELLSCHAFT, Getzersdorf bei Traismauer (AT)

(72) Inventors: Eva-Maria Binder, Tulln (AT); Barbara Cvak, Vienna (AT); Alois Schiessl, Vienna (AT); Georg Häubl, Vienna (AT)

(73) Assignee: ERBER AKTIENGESELLSCHAFT, Getzersdorf bei Traismauer (AT)

( * ) Notice: Subject to any disclaimer, the term of this patent is extended or adjusted under 35 U.S.C. 154(b) by 378 days.

(21) Appl. No.: 15/316,908

(22) PCT Filed: Jun. 3, 2015

(86) PCT No.: PCT/AT2015/000083
§ 371 (c)(1),
(2) Date: Dec. 7, 2016

(87) PCT Pub. No.: WO2015/188205
PCT Pub. Date: Dec. 17, 2015

(65) Prior Publication Data
US 2017/0099862 A1     Apr. 13, 2017

(30) Foreign Application Priority Data
Jun. 12, 2014 (AT) .............................. GM 251/2014

(51) Int. Cl.
*A23L 5/20* (2016.01)
*G01N 33/02* (2006.01)
*G01N 1/40* (2006.01)

(52) U.S. Cl.
CPC ................... *A23L 5/23* (2016.08); *A23L 5/20* (2016.08); *G01N 1/4055* (2013.01); *G01N 33/02* (2013.01);
(Continued)

(58) Field of Classification Search
CPC ......... A23V 2002/00; A23L 5/20; A23L 5/23; G01N 33/02; G01N 1/4055; G01N 2001/4061; G01N 33/025
See application file for complete search history.

(56) References Cited

U.S. PATENT DOCUMENTS

| | | | |
|---|---|---|---|
| 6,773,737 B1 * | 8/2004 | Roselle | A23B 7/154 426/335 |
| 2005/0142254 A1 | 6/2005 | Yabe et al. | |
| 2005/0287682 A1 | 12/2005 | Lizzi et al. | |

OTHER PUBLICATIONS

USGS, Agricultural Contaminants, https://www.usgs.gov/mission-areas/water-resources/science/agricultural-contaminants?qt-science_center_objects=0#qt-science_center_objects, retrieved online Mar. 14, 2019. (Year: 2019).*

(Continued)

*Primary Examiner* — Hong T Yoo
(74) *Attorney, Agent, or Firm* — Jacobson Holman PLLC

(57) ABSTRACT

In a method for extracting contaminants from agrarian products or foods or animal feeds containing agrarian products, comprising contacting a solvent for the contaminants with the agrarian products containing or having adsorbed the contaminants, or the foods or animal feeds, and at least one extraction buffer in an optionally closable mixing vessel, the extraction buffer, which is contained in a film soluble in the solvent and is supplemented with at least one surfactant, in particular nonionic surfactant, and the contaminated agrarian product or food or animal feed are contacted with cold water as solvent in the mixing vessel, and the extraction buffer and the contaminants are brought into solution by (Continued)

agitating or stirring in the mixing vessel; and apparatus therefor.

12 Claims, 2 Drawing Sheets

(52) U.S. Cl.
CPC ........ *G01N 33/025* (2013.01); *A23V 2002/00* (2013.01); *G01N 2001/4061* (2013.01)

(56) References Cited

OTHER PUBLICATIONS

Sigma-Aldrich, Agricultural Contaminants, https://www.sigmaaldrich.com/analytical-chromatography/air-monitoring/applications/agricultural-contaminants.html , retrieved online Mar. 14, 2019. (Year: 2019).*
Chat, Jennifer, Understanding the Definition of an Agricultural Product, https://www.thebalancesmb.com/what-is-an-agricultural-product-2538211, retrieved online Mar. 14, 2019. (Year: 2019).*
Merriam-Weber, quantitative , http//www.merriam-webster.com/dictionary/quantitative (Year: 2020).*
Barkai-Golan, R. and N. Paster, Mouldy fruits and vegetables as a source of mycotoxins: part 1, Wold Mycotoxin Journal, May 2008, 1(2): 147-159. (Year: 2008).*
International Search Report, dated Sep. 8, 2015 (2 pages).
Rudolf Krska et al., "Rapid test strips for analysis of mycotoxins in food and feed", Analytical and Bioanalytical Chemistry, vol. 393, No. 1, Oct. 21, 2008, cited in the ISR (5 pages).

* cited by examiner

METHOD FOR EXTRACTING CONTAMINANTS FROM AGRARIAN PRODUCTS AND APPARATUS THEREFOR

BACKGROUND OF THE INVENTION

The present invention relates to a method for extracting contaminants from agrarian products or foods or animal feeds containing agrarian products, comprising contacting a solvent for the contaminants with the agrarian products containing or having adsorbed the contaminants, or the foods or animal feeds, and at least one extraction buffer in an optionally closable mixing vessel, and apparatus for extracting contaminants from agrarian products or from the surfaces of agrarian products, or foods or animal feeds containing agrarian products, including an optionally closable mixing vessel.

Agrarian products or foods or feeds containing agrarian products are frequently polluted or loaded with contaminants such as mycotoxins, allergens or GMOs (genetically modified oranisms), which contaminants or loadings with mycotoxins, allergens or GMOs not only result in considerable economic losses, but above all may also significantly affect the health of end users. Mycotoxins are especially hazardous, in particular because they exhibit an extremely high stability to chemical and physical influences, e.g. temperature, such that they will still be frequently detectable in substantially unchanged concentrations, and may exert their noxious effects on the end users, even after the processing of agrarian products to foods or feeds. Allergenic contaminants may trigger allergic reactions to anaphylactic shocks in person suffering from respective allergies. The admixture of GMO agrarian products to foods is forbidden by law in many countries, and food producers have to guarantee that no such contaminants are contained in the foods.

Concerning the harmful effects of mycotoxins, a carcinogenic action was discovered in some of them, while others lead to development disorders of individuals to whom foods or feeds contaminated with mycotoxins have been administered, or they show, for instance, a strong estrogenic activity, which is why they may cause hormonal disorders, or it was finally found that they may also contribute to an increase in the miscarriage rates of animals.

Other contaminants such as genetically modified organisms (GMOs) may also have adverse effects, the latter frequently not yet having been fully identified due to the lack or incompleteness of long-term studies.

A further problem, for instance in the delivery of agrarian products, arises in the examination as to whether a delivered batch is free of undesired contaminants such as mycotoxins or GMOs, or whether, and if so to what extent and what kind of, contaminants such as mycotoxins or GMOs are actually contained. In conventional methods, undesired contaminants are dissolved out of the agrarian products by their analytics, using organic solvents such as ethanol, methanol, ethyl acetate, chloroform, acetonitrile or aqueous solutions thereof. At present, samples of the supplied grain are thus usually taken at granaries, in particular in the USA and also in Europe, to which end the grain is ground and subseduently tested for different parameters. Such preliminary examinations involve problems not only with regard to that no or only limited labs and equipment are usually available for the detection of noxious substances at storage facilities for agrarian products, either for cost reasons or due to the fact that such granaries usually do not constitute large enterprises in which qualified personnel and installations for the detection of noxious substances are permanently available or can be kept in stock, respectively, but above all with regard to that the grain is only allowed to be unloaded from the delivering trucks when all of the required tests have been performed and the limit values required by law have not been exceeded.

Examinations are further complicated by the fact that there are a plurality of different mycotoxins, which cannot be extracted from the agrarian products all by the same solvent(s) or solvent mixture(s) or extractant mixture(s), so that, for the test alone, a plurality of different solvents, test strips and the like have to be kept in store, for instance at a granary, in order to be able to perform preliminary tests in respect to a possible or definite contamination with mycotoxins. As a result, trucks carrying grain batches have to undergo various tests prior to unloading in order to prevent agrarian products possibly loaded with mycotoxins from entering the food and feed industries, which renders decontamination altogether more expensive. For the above-mentioned reasons, it is therefore particularly important to enable the whole test procedure to be performed as simply and rapidly as possible on batches as small as possible, since the unloading of grain from a truck will, not be permitted before all tests have been carried out and where the legal limit values have not been exceeded.

From US 2005/0287682 A1 a method can be taken, in which a container such as a Petri dish, a micro-well or a tube is filled with a first substance and a readily soluble film is subsequently disposed above said first substance in the interior of the container, said film providing a sear for said first substance relative to the environment or further substances optionally provided in the interior of the container.

BRIEF SUMMARY OF THE INVENTION

The present invention aims to provide a method that enables the reliable quantitative extraction of mycotoxins from agrarian products, or foods or feeds containing agrarian products, without simultaneously introducing into the samples substances that are hazardous or harmful to end users, such as organic solvents or other hazardous reactants.

To solve this object, the method according to the invention is substantially conducted in such a manner that the extraction buffer, which is contained in a film soluble in the solvent and is supplemented with at least one surfactant, in particular nonionic surfactant, and the contaminated agrarian product or food or animal feed are contacted with cold water as solvent in the mixing vessel, and the extraction buffer and the contaminants are brought into solution by agitating or stirring in the mixing vessel. In that the extraction buffer, which is contained in a film soluble in a solvent and is supplemented with at least one surfactant, is brought into solution with water by agitating or stirring in the mixing vessel, it has become possible to reduce as far as possible the number of reagents to be kept in stock, and such a procedure will, in particular, ensure that no professionally qualified personnel will have to be present during such detections, especially in small enterprises, since even amateurs are readily believed to be capable of dissolving a bag containing all solvents suitable for extracting contaminants.

In that the method is, moreover, conducted such that the foods or animal feeds are also contacted with cold water as solvent in the mixing vessel, it has become possible to mix all components in one and the same reaction vessel, in particular a beaker, whereupon the mycotoxins adsorbed by the agrarian products are quantitatively dissolved or detached and the question of whether, and what amounts of, mycotoxins are contained on the surfaces of the agrarian products can subsequently be immediately clarified, for instance by applying a quick test.

In that, as in correspondence with a further development of the method according to the invention, the method is conducted such that water having a temperature between 8° C. and 25° C., in particular distilled water, is used, it will, moreover, be avoided to use heating means or devices for heating the water such that both the energy and the time required for performing the method can be kept extremely low. Although the method is fully operational when using tap water, it is preferred to use distilled water, in particular if it is to be ensured that no harmful or interfering substances such as nitrates are eventually introduced along with the solvents.

If, as in correspondence with a further development of the invention, at least one buffer selected from the group consisting of borate buffers having a pH of 8.5, carbonate buffers having a ph of 9.1, citrate buffers having a pH of 7.1, phosphate buffers having a pH of 7.4 and Tris/HCl buffer having a ph of 7.4, the quantitative extraction of all known mycotoxins from the agrarian products will be successful without having to use chemicals that are harmful to human beings and animals, such a mode of operation at the same time allowing for the extraction of mycotoxins from said products to be performed at room temperature, i.e. temperatures between 15° C. and 25° C., thus providing an energy-saving method to be rapidly performed without requiring any chemicals harmful to human beings and animals.

If, as in correspondence with a further development of the invention, the method is conducted such that the extraction buffer is used at a concentration of between 10 mM and 100 mM, it is ensured that the mycotoxins are quantitatively dissolved, thus enabling the qualitative detection of the presence thereof and a quantitative detection relating to the content of contaminants, so that it can be decided in situ whether, for instance, a batch of delivered agrarian products will have to be subjected to a further treatment for eliminating mycotoxins or whether it can be directly reused, since, for instance, the load of mycotoxins or contaminants is so low that it lies below a range harmful to human beings or animals.

In that, as in correspondence with a further development of the invention, the method is conducted such that the extraction buffer is mixed with a powdery carrier, in particular an inert silicate powder such as high-purity silicic acid, it has become possible to maintain the solubility properties of the extraction buffer at a constantly good level while, at the same time, significantly improving the processability of the extraction buffer, in particular its selective introduction into the film soluble in a solvent, so as to not only improve said processability but, in particular, enhance the accuracy of the analysis, since also the amount of used extraction buffer is precisely quantifiable.

In that, as in correspondence with a further development of the invention, 0.1 to 1% of a surfactant is added to the extraction buffer, an even more rapid and complete dissolution of the mycotoxins adsorbed on the agrarian products will be enabled in the extraction buffer supplemented with water. In that, furthermore, the surfactant is selected from polyoxyethyelene (23) lauryl ether (BRIJ™ 35 detergent), polyoxyethylene (20) acetyl ether (BRIJ™ 58 detergent), 4-(1,1,3,3-tetramethylbutyl)phenyl-polyethylene glycol (TRITON™ X100 surfactant), (1,1,3,3-tetramethylbutyl) phenyl-polyethylene glycol (TRITON™ X114 detergent), polysorbate 20, polysorbate 80 or sodium dodecyl sulfate, a particularly rapid dissolution of the contaminants, in particular mycotoxins, will be ensured so as to further reduce the time necessary for finding out whether agrarian products, or foods or feeds containing such products, are contaminated with mycotoxins or not.

Particularly rapid and reliable operation is achieved in that, as in correspondence with a further development of the invention, the film soluble in the solvent is used as a bag closed on all sides and containing a buffer comprising at least two of the following components sodium or potassium salts of boric acid, carboxylic acid, citric acid, phosphoric acid, phosphorous acid, TRIS (Tris(hydroxymethyl)-aminomethane) and NaCl, said buffer after dissolution having a molarity of 6 to 250 mM, in particular 10 to 100 mM, and a pH ranging from 6.5 to 9.5, in particular between 7.1 and 9.1. In this connection, a pH deviation of ±0.3 will have no effects on the test result. Such operation ensures that, on the one hand, no optionally noxious organic solvents, or organic solvents that are subsequently difficult to remove, have to be employed, but buffer systems just based on water, which are not harmful to human beings and the environment, that also the used solutions or solutions loaded with mycotoxins are easy to treat, i.e. need not be subjected to complex treatments, as would, for instance, be the case when using organic solvents, that, due to the use of plastic bags closed on all sides and soluble in water, chemicals can, moreover, be safely and reliably handled and dissolved by unskilled personnel, and that, in particular, also the required quantities of solvents, i.e. water, can, for instance, be taken from an imprint on the bag, thus rendering the method extremely time-saving. Finally, the storage of small, tightly closed plastic bags is very simple, requiring neither skilled personnel nor special precautions during storage.

The invention further aims to provide a device that allows for the simple and reliable extraction of contaminants from agrarian products or the surfaces of agrarian products, which device does not require excessive space and can, moreover, be safely and reliably operated even by unskilled personnel. To solve this object, the device or apparatus according to the invention is essentially characterized in that the mixing vessel is comprised of a foldable plastic bag containing an extraction buffer enclosed in a soluble, in particular water-soluble, film. In that the mixing vessel is comprised of a foldable plastic bag containing an extraction buffer enclosed in a soluble, in particular water-soluble, film, a device has been provided, in which an extraction buffer is contained in a bag and which device is also foldable. Such a device enables the direct introduction of the solvent into the plastic container, or plastic bag, and also the addition of the agrarian products to be examined, so as to, for instance, render superfluous the storage of vessels such as beakers, glasses, Erlenmeyer flasks and the like, in which such examinations are usually performed.

In that, as in correspondence with a further development of the invention, the plastic bag on one end is closed by welds comprising a tear-open element and the extraction buffer enclosed in the water-soluble film is, moreover, received in the closed plastic bag, it is further ensured that the extraction buffer enclosed in the water-soluble film will not be prematurely enter into contact with moisture and, for instance, be prematurely dissolved. In that the plastic bag is, moreover, provided with a tear-open element on one end, it has become possible, by simply tearing open the plastic bag, to provide the required mixing vessel already comprising within the water-soluble film an amount of extraction buffer suitable for the size of the vessel, in particular bag.

In that, as in correspondence with a further development of the invention, the device is configured such that one end of the plastic bag is formed with a double bottom and that the film facing the interior of the plastic bag and forming said double bottom of the plastic bag is comprised of the water-soluble film enclosing the extraction buffer, a device that is particularly easy to handle has been provided, into which only water and the agrarian products to be examined have to be introduced in order to be able to perform an examination as to the presence of contaminants, in particular mycotoxins, on the surfaces of the agrarian products.

According to a further development of the invention, the device is configured such that the tear-open element is designed as a plastic rod, in particular stirring rod, so as to ensure, by simple stirring in the interior of the plastic bag after the addition of water and the addition of the agrarian products, the complete and safe dissolution of the extraction buffer and the detachment of mycotoxins possibly present on the agrarian products.

In order to facilitate operation and, in particular, enable also unskilled personnel to perform correct examinations, the plastic bag, according to a further development of the invention, is provided with a scale in a manner known per se. By providing such a scale, even unskilled personnel will be able to precisely introduce into the plastic bag the exact amount of solvent in order to perform a reliable and, in particular, also quantitative examination.

BRIEF DESCRIPTION OF THE DRAWINGS

In the following, the invention will be explained in more detail by way of exemplary embodiments illustrated in the drawing. Therein.

DETAILED DESCRIPTION OF THE INVENTION

Figure 1:
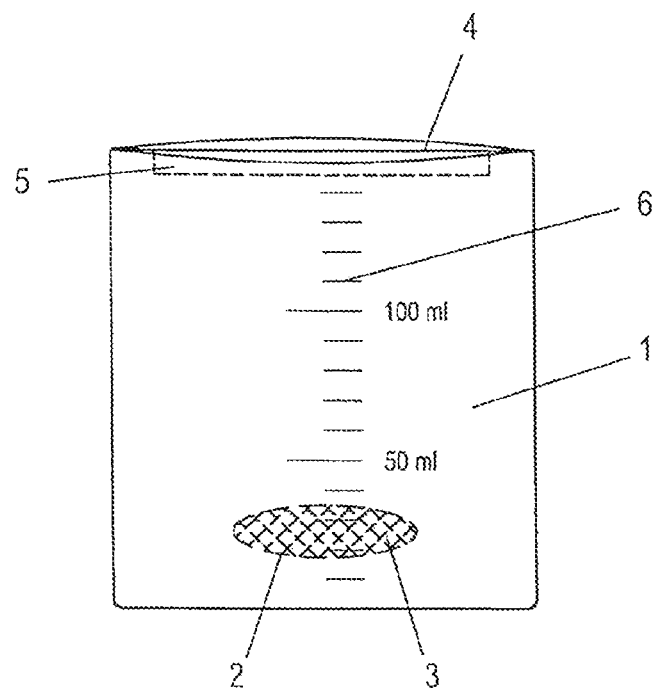
FIG. 1 illustrates a device according to the invention containing an extraction buffer enclosed in a water-soluble film.

In detail, FIG. 1 illustrates a mixing vessel comprised of a plastic bag 1, in whose interior an extraction buffer 3 received in a water-soluble film 2 is contained. The extraction buffer can be supplemented with high-purity silicic acid as a carrier so as to improve its filling and homogenization, yet without influencing its extraction properties. In the illustration according to FIG. 1, the bag 1 is shown in the closed state with a tear-open element 4 provided on its upper end, in which a rod-shaped element 5 is enclosed, which rod-shaped element 5 is also torn off when opening the bag 1 and can subsequently be removed from the torn-off part of the tear-open element 4 and, for instance, be used as a stirring rod. The bag 1, moreover, comprises a scale 6 on its outer side to enable the determination of the exact amount of water to be filled in when in use.

Figure 2:
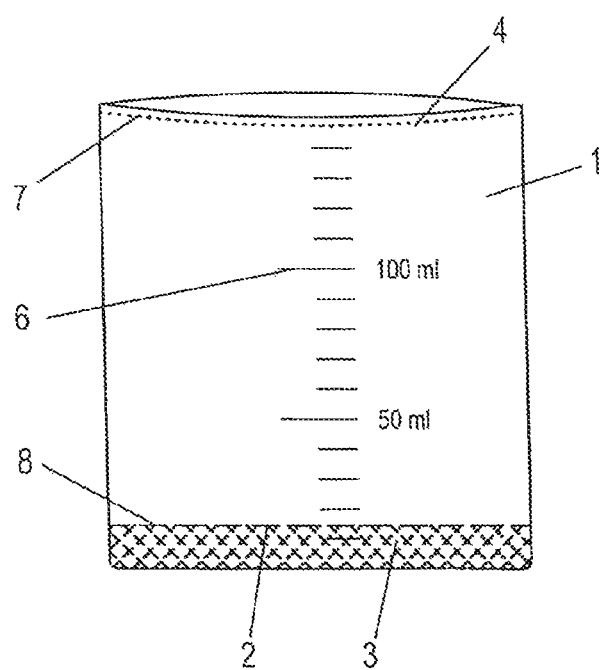
FIG. 2 illustrates another configuration of the device of FIG. 1, in which the extraction buffer is provided in the double bottom of a plastic bag.

FIG. 2 depicts another variant of a device according to the invention, in which the reference numerals have been retained as far as possible. The bag 1 is again provided with a scale 6, and on its upper end additionally comprises a tear-open element 4 designed as a tear-open edge 4. In the illustration according to FIG. 2, the tear-open element 4 is provided with a perforation 7, whereby, when opening the bag 1, the bag 1 can be opened by simply pulling off the upper tear-open element 4 along said perforation 7. The lower region of the bag 1 is, moreover, formed with a double bottom 8, the extraction buffer 3 being enclosed between the lower end of the bag 1 and the double bottom 8. In use, such a bag 1 is opened, water is filled in as far as to the desired mark, and the soluble film 2 covering the extraction buffer 3 as a double bottom 8 is dissolved either by careful shaking of the bag or by stirring in the interior of the bag, thus causing the buffer to come into contact with the solvent. After the extraction buffer 3 has been dissolved, the agrarian product 9 to be examined is filled into the interior of the bag 1 and either allowed to rest for some minutes or further stirred in order to detach as rapidly as possible the contaminants contained on the surface of the product 9. It goes without saying that the agrarian product and the buffer to be dissolved can be filled in simultaneously or in any order. After this, it will do to detect, for instance by a strip test, whether, or in the case of a quantitative strip test what amounts and/or kinds of, contaminants or mycotoxins were present on the surface of the agrarian product 9.

Figure 3:
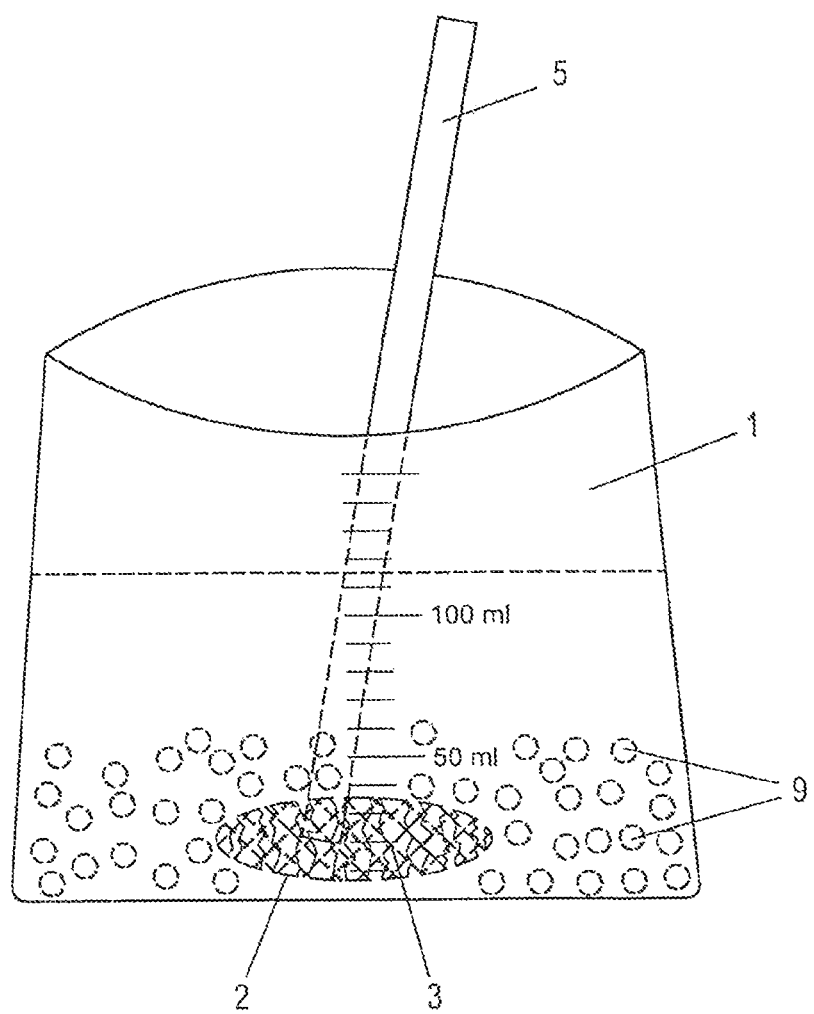
FIG. 3 depicts the device of FIG. 1 in the opened state, when in use.

FIG. 3 depicts the bag 1 of FIG. 1, illustrating the bag in the torn-open state with the extraction buffer 3 already dissolved, the water-soluble film 2 already showing cracks and destructions, and the agrarian product 9 to be examined having, moreover, been filled in along with water as solvent. For dissolving, or facilitating the dissolution of, the extraction buffer 3 and detaching the contaminants from the surface of the agrarian product 9, the stirring rod 5 is used for stirring in the interior of the bag 1.

After the complete dissolution of the extraction buffer 3, a conventional strip test can, for instance, be used to examine the presence of contaminants.

Example 1

Detection of Different Mycotoxins in Maize Samples

The Tables below show the detection of different mycotoxins in maize samples when tested with different buffers comprising salts and surfactants, and a summary of the detection of toxins in the phosphate buffer system (each at concentrations of 10 mM and 100 mM), performed with ELISA:

carbonate buffer, pH 8.5
carbonate buffer, pH 9.1,
citrate buffer, pH 7.1,
phosphate buffer, pH 7.4 and
Tris/HCl buffer, pH 7.5.

In the Tables, the following detection ratios are indicated:

| Results of strip tests (LFDs): | |
|---|---|
| Result | Detection |
| (+) | <30% |
| + | 30-50% |
| ++ | 50-80% |
| +++ | >80% |

Aflatoxins:

Table 1 shows the detection of aflatoxins in maize samples. Different buffer combinations (salt+surfactant) were tested.

TABLE 1

| | Aflatoxins | | | | | | |
|---|---|---|---|---|---|---|---|
| Buffer [mM] | Tween 20 [%] 0.1/1 | Tween 80 [%] 0.1/1 | Triton X100 [%] 0.1/1 | Triton X114 [%] 0.1/1 | Brij 35 [%] 0.1/1 | Brij 58 [%] 0.1/1 | SDS [%] 0.1/1 |
| Borate 10 mM | ++/++ | ++/+++ | ++/++ | ++/+++ | ++/++ | ++/+++ | +++/++ |
| Borate 100 mM | ++/++ | ++/++ | ++/++ | ++/++ | ++/++ | ++/++ | +++/++ |
| Carbonate 10 mM | ++/+++ | ++/+++ | ++/++ | ++/+++ | ++/++ | ++/+++ | +++/++ |
| Carbonate 100 mM | ++/+++ | ++/+++ | ++/++ | ++/+++ | ++/++ | ++/++ | +++/++ |
| Citrate 10 mM | +/+ | +/++ | +/++ | +/++ | +/++ | +/++ | ++/+ |
| Citrate 100 mM | +/+ | +/+ | +/+ | +/+ | +/+ | +/+ | ++/+ |
| Phosphate 10 mM | ++/+++ | ++/+++ | ++/++ | ++/++ | ++/+++ | ++/+++ | +++/++ |
| Phosphate 100 mM | ++/+++ | ++/++ | ++/++ | ++/++ | ++/+++ | ++/+++ | +++/++ |
| Tris/HCl 10 mM | ++/++ | ++/++ | ++/++ | ++/++ | ++/++ | ++/++ | +++/++ |
| Tris/HCl 100 mM | ++/++ | ++/++ | ++/++ | ++/++ | ++/++ | ++/++ | +++/++ |

Deoxynivalenol:

Table 2 shows the detections of deoxynivalenol in maize samples. Different buffer combinations (salt+surfactant) were tested.

TABLE 2

| | Deoxynivalenol | | | | | | |
|---|---|---|---|---|---|---|---|
| Buffer [mM] | Tween 20 [%] 0.1/1 | Tween 80 [%] 0.1/1 | Triton X100 [%] 0.1/1 | Triton X114 [%] 0.1/1 | Brij 35 [%] 0.1/1 | Brij 58 [%] 0.1/1 | SDS [%] 0.1/1 |
| Borate 10 mM | +++/+++ | +++/+++ | +++/+++ | +++/+++ | +++/+++ | +++/+++ | +++/++ |
| Borate 100 mM | +++/+++ | +++/+++ | +++/+++ | +++/+++ | +++/+++ | +++/+++ | +++/++ |
| Carbonate 10 mM | +++/+++ | +++/+++ | +++/+++ | +++/+++ | +++/+++ | +++/+++ | +++/++ |
| Carbonate 100 mM | +++/+++ | +++/+++ | +++/+++ | +++/+++ | +++/+++ | +++/+++ | +++/++ |
| Citrate 10 mM | ++/++ | ++/++ | ++/++ | ++/++ | ++/++ | ++/++ | ++/+ |
| Citrate 100 mM | ++/++ | ++/++ | ++/++ | ++/++ | ++/++ | ++/++ | ++/+ |
| Phosphate 10 mM | +++/+++ | +++/+++ | +++/+++ | +++/+++ | +++/+++ | +++/+++ | +++/++ |
| Phosphate 100 mM | +++/+++ | +++/+++ | +++/+++ | +++/+++ | +++/+++ | +++/+++ | +++/++ |
| Tris/HCl 10 mM | +++/+++ | +++/+++ | +++/+++ | +++/+++ | +++/+++ | +++/+++ | +++/++ |
| Tris/HCl 100 mM | +++/+++ | +++/+++ | +++/+++ | +++/+++ | +++/+++ | +++/+++ | +++/++ |

Fumonisins:

Table 3 shows the detections of fumonisins in maize samples. Different buffer combinations (salt+surfactant) were tested.

TABLE 3

| | Fumonisins | | | | | | |
|---|---|---|---|---|---|---|---|
| Buffer [mM] | Tween 20 [%] 0.1/1 | Tween 80 [%] 0.1/1 | Triton X100 [%] 0.1/1 | Triton X114 [%] 0.1/1 | Brij 35 [%] 0.1/1 | Brij 58 [%] 0.1/1 | SDS [%] 0.1/1 |
| Borate 10 mM | ++/+++ | ++/+++ | ++/+++ | ++/+++ | ++/(+) | ++/(+) | ++/(+) |
| Borate 100 mM | ++/+++ | ++/+++ | ++/+++ | ++/+++ | ++/(+) | ++/(+) | ++/(+) |
| Carbonate 10 mM | ++/+++ | ++/+++ | ++/+++ | ++/+++ | ++/(+) | ++/(+) | ++/(+) |
| Carbonate 100 mM | ++/+++ | ++/+++ | ++/+++ | ++/+++ | ++/(+) | ++/(+) | ++/(+) |
| Citrate 10 mM | ++/++ | ++/++ | ++/++ | ++/++ | ++/(+) | ++/(+) | ++/(+) |
| Citrate 100 mM | ++/++ | ++/++ | ++/++ | ++/++ | ++/(+) | ++/(+) | ++/(+) |
| Phosphate 10 mM | ++/+++ | ++/+++ | ++/+++ | ++/+++ | ++/(+) | ++/(+) | ++/(+) |
| Phosphate 100 mM | ++/+++ | ++/+++ | ++/+++ | ++/+++ | ++/(+) | ++/(+) | ++/(+) |
| Tris/HCl 10 mM | ++/+++ | ++/+++ | ++/+++ | ++/+++ | ++/(+) | ++/(+) | ++/(+) |
| Tris/HCl 100 mM | ++/+++ | ++/+++ | ++/+++ | ++/+++ | ++/(+) | ++/(+) | ++/(+) |

Zearalenones:

Table 4 shows the detections of zearalenones in maize samples. Different buffer combinations (salt+surfactant) were tested.

TABLE 4

| | Zearalenone: | | | | | | |
|---|---|---|---|---|---|---|---|
| Buffer [mM] | Tween 20 [%] 0.1/1 | Tween 80 [%] 0.1/1 | Triton X100 [%] 0.1/1 | Triton X114 [%] 0.1/1 | Brij 35 [%] 0.1/1 | Brij 58 [%] 0.1/1 | SDS [%] 0.1/1 |
| Borate 10 mM | +++/++ | +++/++ | +++/++ | +++/++ | +++/++ | +++/++ | +++/+ |
| Borate 100 mM | +++/++ | +++/++ | +++/++ | +++/++ | +++/++ | +++/++ | +++/+ |
| Carbonate 10 mM | ++/+++ | ++/+++ | +++/++ | ++/+++ | +++/++ | ++/+++ | +++/+ |
| Carbonate 100 mM | ++/+++ | ++/+++ | +++/++ | ++/+++ | +++/++ | ++/+++ | +++/+ |
| Citrate 10 mM | +/+ | +/+ | +/+ | +/+ | +/+ | +/+ | ++/+ |
| Citrate 100 mM | +/+ | +/+ | +/+ | +/+ | +/+ | +/+ | ++/+ |
| Phosphate 10 mM | +++/++ | +++/++ | +++/++ | +++/++ | +++/++ | +++/++ | +++/+ |
| Phosphate 100 mM | +++/++ | +++/++ | +++/++ | +++/++ | +++/++ | +++/++ | +++/+ |
| Tris/HCl 10 mM | ++/+++ | ++/+++ | ++/+++ | ++/+++ | +++/++ | ++/+++ | +++/+ |
| Tris/HCl 100 mM | ++/+++ | ++/+++ | ++/+++ | ++/+++ | +++/++ | ++/+++ | +++/+ |

TABLE 5

Summary of LFD results:

| TOXIN<br>PBS buffer | Tween 20 [%]<br>0.1/1 | Tween 80 [%]<br>0.1/1 | Triton X100 [%]<br>0.1/1 | Triton X114 [%]<br>0.1/1 | Brij 35 [%]<br>0.1/1 | Brij 58 [%]<br>0.1/1 | SDS [%]<br>0.1/1 |
|---|---|---|---|---|---|---|---|
| Aflatoxins 10 mM | ++/++ | ++/++ | ++/++ | ++/++ | ++/+++ | ++/++ | +++/+ |
| Aflatoxins 100 mM | ++/++ | ++/++ | ++/++ | ++/++ | ++/+++ | ++/++ | +++/+ |
| Deoxynivalenol 10 mM | +++/+ | +++/+ | +++/++ | +++/+ | +++/++ | +++/+ | +++/+ |
| Deoxynivalenol 100 mM | +++/+ | +++/+ | +++/++ | +++/+ | +++/++ | +++/+ | +++/+ |
| Fumonisins 10 mM | ++/++ | ++/++ | ++/+++ | ++/++ | ++/(+) | ++/(+) | ++/(+) |
| Fumonisins 100 mM | ++/++ | ++/++ | ++/+++ | ++/++ | ++/(+) | ++/(+) | ++/(+) |
| Zearalenones 10 mM | ++/+++ | +++/+ | +++/++ | +++/+ | +++/++ | ++/+ | +++/+ |
| Zearalenones 100 mM | ++/+++ | +++/+ | +++/++ | +++/+ | +++/++ | ++/+ | +++/+ |

It follows from the above Tables that the LFD and ELISA results are comparable, and the different buffer systems and different surfactants and concentrations are applicable to the extraction method, yielding reliable results.

Example 2

Extraction of Food Allergens Using an Extraction Buffer Contained in Water-Soluble Films Tris/HCl and a PBS buffer, each shrink-wrapped in a water-soluble film, are introduced into a plastic container and supplemented with cold tap water until 100 mM, 150 mM, 200 mM and 250 mM solutions have each formed. The solutions had pH values ranging between 6.5 and 8.8 as a function of the employed buffer.

Both extraction buffers enabled the quantitative extraction of the following food allergens, using all four different concentrations: β-lactoglobulin, casein, cashew nut, egg white, peanut, fish, hazelnut, crustaceans, lupin, almond, milk, ovalbulmin, pistachio, mustard, sesame, soy, walnut.

Example 3

Extraction of Genetically Modified Organism Using an Extraction Buffer Contained in Water-Soluble Films Tris/HCl, PBS and a borate buffer, each shrink-wrapped in a water-soluble film along with Tween or Triton and silicagel, are introduced into a plastic container and supplemented with cold tap water until 100 mM, 150 mM, 200 mM and 250 mM solutions have each formed.

Both extraction buffers enabled the quantitative extraction of the following genetically modified organisms, and the quantification of the results by Statfax® and Chromate® readers, using all four different concentrations: RUR, Cry1F, Cry1AB, Cry3bb, LL, Cry34AB1, VIP, Btk, BR, B2R, EPSPS, DAS Cry1Ac.

The invention claimed is:

1. A method for quantitatively extracting contaminants selected from the group consisting of mycotoxins, allergens and genetically modified organisms from agrarian products or foods or animal feeds containing agrarian products, comprising the step of:
    providing the agrarian products or foods or animal feeds containing agrarian products that contain or absorbed contaminants selected from the group consisting of mycotoxins, allergens and genetically modified organisms,
    providing at least one extraction buffer in a film that is water soluble,
    contacting distilled water, the at least one extraction buffer, at least one surfactant and a powdery carrier with the agrarian products or the foods or animal feeds containing agrarian products, in a closable mixing vessel,
    closing the closable mixing vessel,
    agitating or stirring the mixing vessel so that the film is dissolved and the at least one extraction buffer and the contaminants are brought into solution, and
    extracting the contaminants from the agrarian products or foods or animal feeds containing agrarian products;
    wherein the distilled water has a temperature 8° C. and 25° C.; and
    wherein the at least one extraction buffer selected from the group consisting of borate buffers, carbonate buffers, citrate buffers, phosphate buffers and Tris/HCl buffer.

2. The method according to claim 1, wherein the extraction buffer is used at a concentration of between 10 mM and 100 mM.

3. The method according to claim 1, wherein an inert silicate powder is used as said powdery carrier.

4. The method according to claim 3, wherein the surfactant is selected from polyoxyethyelene lauryl ether, polyoxyethylene acetyl ether, 4-(1,1,3,3-tetramethylbutyl)phenyl-polyethylene glycol, (1,1,3,3-tetramethylbutyl)phenyl-polyethylene glycol, or sodium dodecyl sulfate.

5. The method according to claim 3, wherein the inert silicate powder is a high purity silicic acid.

6. The method according to claim 1, wherein the at least one buffer comprises at least two of the following components: sodium or potassium salts of boric acid, carboxylic acid, citric acid, phosphoric acid, phosphorous acid, TRIS (Tris(hydroxymethyl)-aminomethane) and NaCl, said buffer after dissolution having a molarity of 6 to 250 mM, and a pH ranging from 6.5 to 9.5.

7. The method according to claim 1, wherein the surfactant is non-ionic.

8. The method according to claim 1, wherein the buffer after dissolution having a molarity of 10 to 100 mM, and a pH ranging between 7.1 and 9.1.

9. The method according to claim 1, wherein the at least one extraction buffer selected from the group consisting of borate buffers having a pH of 8.5, carbonate buffers having a pH of 9.1, citrate buffers having a pH of 7.1, phosphate buffers having a pH of 7.4 and Tris/HCl buffer having a pH of 7.4.

10. The method according to claim 1, wherein the agrarian product is maize and the contaminant is mycotoxins, aflatoxins, deoxynivalenol, fumonisins or zearalenones.

11. The method according to claim 1, wherein the surfactant is selected from polyoxyethyelene lauryl ether, polyoxyethylene acetyl ether, 4-(1,1,3,3-tetramethylbutyl)phenyl-polyethylene glycol, (1,1,3,3-tetramethylbutyl)phenyl-polyethylene glycol, or sodium dodecyl sulfate; and wherein the at least one extraction buffer selected from the group consisting of borate buffers having a pH of 8.5, carbonate buffers having a pH of 9.1, citrate buffers having a pH of 7.1, phosphate buffers having a pH of 7.4 and Tris/HCl buffer having a pH of 7.4.

12. The method according to claim 11, wherein the method further comprises the step of detecting an amount of the contaminant.

* * * * *